US00PP37188P2

(12) United States Plant Patent
Hansen

(10) Patent No.: US PP37,188 P2
(45) Date of Patent: Dec. 30, 2025

(54) ***HEUCHERELLA* PLANT NAMED 'Shadow Tag'**

(50) Latin Name: x ***Heucherella* (*Heuchera* times *Tiarella*)**
Varietal Denomination: Shadow Tag

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,347

(22) Filed: Nov. 25, 2024

(51) Int. Cl.
*A01H 5/12* (2018.01)
*A01H 6/80* (2018.01)

(52) U.S. Cl.
USPC ..... Plt./441

(58) Field of Classification Search
USPC ..... Plt./441
CPC ... A01H 5/02; A01H 5/12; A01H 5/00; A01H 6/80
See application file for complete search history.

(56) References Cited

PUBLICATIONS

Griffin 2024 retrieved on Feb. 24, 2025 at https://www.griffins.com/viewCategory?c=productSearch&contextList=eJytzUEKwjAQheG7zLrOAbqLNgshpCWpiMuQDhooSZimSCm9u90orsXtD%2B97K5xcoXviBeoVyplJavDvVIHnUliD22unhO4tmrbtZYOdNFLrs1AWr0LhTQpj2otuYKs%2B%2B0MeXSwTckqFBszEFGNw44RPN%2BJCjjnNcfjjc%2BY0zL7YnfaPL . . . one page (Year: 2024).*
BFG Supply Walters Gardens 2025 Program, retrieved on Feb. 24, 2025 at https://www.bfgsupply.com/media/9082/2025-walters-product-program.pdf, pp. 1-5, 11 (total 6 pages). (Year: 2025).*

* cited by examiner

*Primary Examiner* — June Hwu

(57) ABSTRACT

The new hybrid x *Heucherella* plant named 'Shadow Tag' with palmately-lobed leaves that are shallowly dissected into five to seven main. Foliage color is distinctly silvery-green and starts in the spring with burgundy surrounding the center veins. The flower effect is purplish-pink in moderately densely-branched panicles beginning in late May. The plant is useful for landscaping as a specimen color, en masse, or as a container plant.

1 Drawing Sheet

Botanical denomination: x *Heucherella* (*Heuchera* times *Tiarella*).

Cultivar designation: 'Shadow Tag'.

STATEMENT REGARDING PRIOR DISCLOSURES UNDER 37 CFR 1.77(B)(6)

The first offer for sale of the new plant anywhere in the world was on Jul. 8, 2024, by Walters Gardens, Inc. The first description of the new plant was a brief description and a photograph on a website operated by Walters Gardens, Inc. on Dec. 1, 2024. This was followed by a small photograph and brief description in the "Walters Gardens 2024-2025 Catalog" first distributed on May 23, 2024. Walters Gardens, Inc. obtained the new plant and all information about the new plant from the inventor. No plants of x *Heucherella* 'Shadow Tag' have been sold in this country or anywhere in the world, nor has any disclosure of the new plant been made, more than one year prior to the filing date of this application, and such sale or disclosure within one year was either derived directly or indirectly from the inventor and thus should be considered a 35 U.S.C. § 102(b) exception.

The present invention relates to a new and distinct intergeneric hybrid between Coral Bells and Foam Flower, both in the Saxifragaceae family and given the cultivar name of 'Shadow Tag' with the combined generic epithet x *Heucherella.* x *Heucherella* 'Shadow Tag' resulted from an intentional cross between the proprietary hybrid *Heuchera* known only by the hybrid number 13-819-1 (not patented) as the female or seed parent and the unreleased, proprietary hybrid known only as *Tiarella* 12-5-4 (not patented) as the male or pollen parent. The cross was hybridized by the inventor at a wholesale perennial nursery in Zeeland, Michigan, USA on May 18, 2021. The new plant was selected from among many other crosses and x *Heucherella* seedlings growing at the same nursery which met the rigorous criteria of excellent foliage, vigor, and habit and was assigned the breeder code of 21-3-8.

x *Heucherella* 'Shadow Tag' has been asexually propagated initially by basal cuttings in 2022 at a nursery in Zeeland, Michigan, and since by sterile shoot tip tissue culture propagation. The resultant asexually propagated plants have remained stable and exhibit the same characteristics as the original plant over multiple generations.

BRIEF SUMMARY OF THE INVENTION x *Heucherella* 'Shadow Tag' differs from its parents as well as all other X *Heucherella* known to the applicant. The most similar cultivars are: x *Heucherella* 'Cracked Ice' U.S. Plant Pat. No. 24,690, 'Galactica' (U.S. Plant patent application Ser. No. 15,530,534 (abandoned), 'Party Time' U.S. Plant Pat. No. 16,181, and 'Pink Fizz' U.S. Plant Pat. No. 26,947.

Compared with the female parent the new plant has red flowers. The male parent has more white flowers flatter and lacks the silver overlay of the foliage.

'Cracked Ice' has foliage that is more dissected with a slight ruffle, the color is more silver with dark purplish-green around the veins, and the flowers are white. 'Galactica' has narrower and more dissected leaf lobes with darker mahogany undertones and flowers of lighter creamy pink. 'Party Time' has smaller leaves with longer lobes with more rounded apices. 'Pink Fizz' has smaller foliage that has more divided with long apical lobes and the flowering is more profuse over a longer period.

The new plant differs from all *Heuchera*, x *Heucherella*, and *Tiarella* known to the inventor in the following combined traits:

1. The large foliage that is distinctly silver and green with chartreuse and burgundy surrounding the center veins earlier in the season;
2. Leaves have shallowly dissected lobes and slight ruffles on the margin;
3. The flower effect is purplish-pink;
4. Habit develops into a large mound with multiple tightly clustered shoots emerging at the base;
5. The plant is more robust, and more heat tolerant than typical x *Heucherella*.

BRIEF DESCRIPTION OF THE DRAWING

The photographs of the new plant demonstrate the overall appearance of the plant including the unique traits. The plant in the photograph is a two-year-old plant grown at a wholesale perennial nursery in Zeeland, Michigan, USA. The colors are as accurate as reasonably possible with color reproductions. Some slight variations of color may occur as a result of lighting quality, intensity, wavelength, and direction or reflection.

Figure 1:
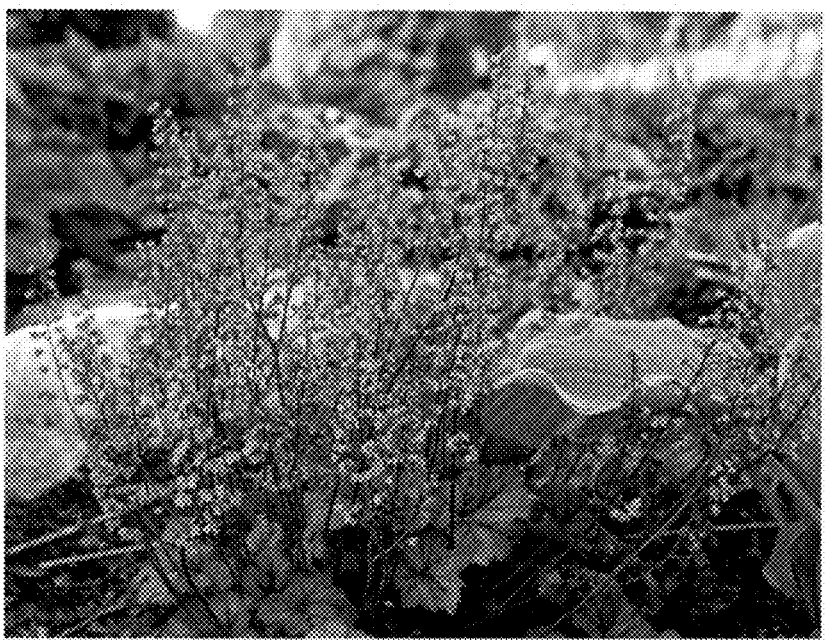
FIG. 1 shows the new plant in full flower in the spring garden.
Figure 2:
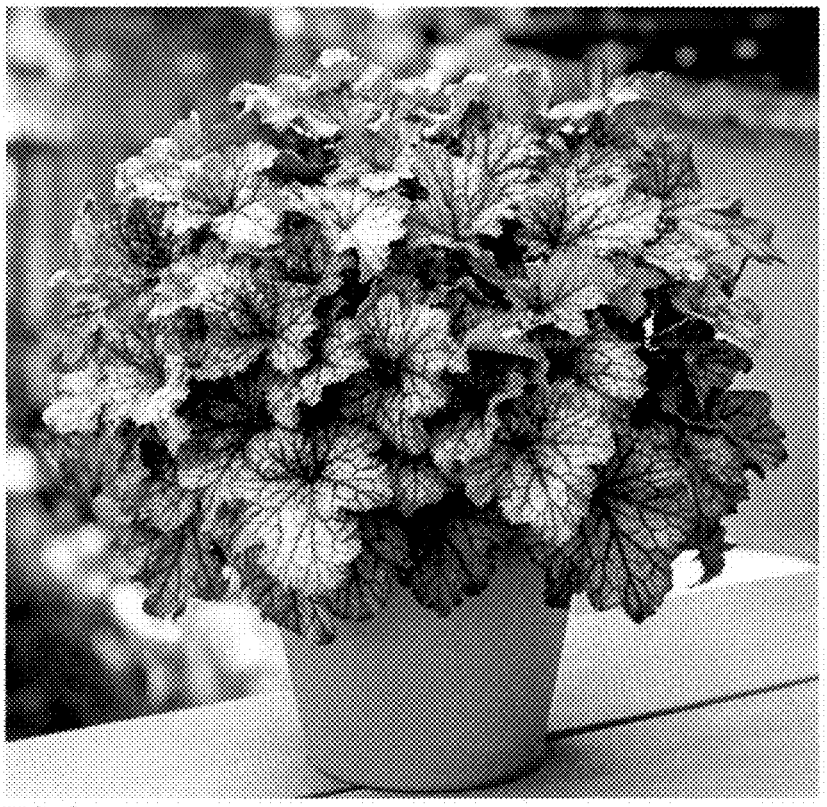
FIG. 2 shows the foliage and habit of a greenhouse contain-grown plant in mid- summer.

DETAILED BOTANICAL DESCRIPTION.

The following description is based on two-year-old plants growing in a partially shaded greenhouse with supplemental water and fertilizer at a wholesale perennial nursery in Zeeland, Michigan, USA. 'Shadow Tag' has not been grown under all possible environments and may phenotypically appear different under different conditions such as light, temperatures, fertilizer, and water, without any difference in genotype. The color descriptions are from the 2015 edition of The Royal Horticultural Society Colour Chart except where common dictionary terms are used.

Parentage: The female or seed parent is the *Heuchera* hybrid 13-819-1; the male or pollen parent was *Tiarella* hybrid 12-5-4;

Plant habit: Hardy herbaceous perennial of tightly compact rhizomes with basal rosette in a rounded mound of foliage; foliage about 25 cm tall and 45 cm across; flowering to about 50 cm tall;

Roots: Fibrous, finely branched; when actively growing near white in color depending on soil type, nearest RHS 158D;

Growth rate: Rapid, rooting from cutting in 2 weeks and finishing in a 3.8-liter container in about 3 months;

Foliage: Palmate; shallowly lobed into five to seven irregular main lobes; sparsely puberulent adaxial and abaxial; lobes dissected to about 1 cm deep from margin; secondary lobes are dissected to about 2 mm to 3 mm deep; matte surface above and below; main and secondary lobes with acute apices; margins serrate and ciliolate; cordate base with lobes imbricate about 1 cm; foliage density dense; glossiness weak; undulation weak;

Foliage size: Blade to about 11 cm wide and 11.5 cm long, average about 8.5 cm wide and 9 cm long; center lobe about 3.5 cm long and about 6.5 cm wide, short;

Foliage margin indentations: Shallowly dissected;

Foliage color: Seasonally variable; spring and young emerging leaves adaxial between RHS 138B and RHS 138A and the center inner palm surrounding the main veins nearest RHS 187A; abaxial spring emerging leaves between RHS 147C and RHS 146C with a moderate undertone surrounding veins nearest RHS 187B; when first flowering through autumn adaxial margin portion and portion surrounding distal veins between RHS NN137A and RHS NN137B, portion between the veins between RHS N138D and RHS 191C; when first flowering through autumn abaxial nearest RHS 148B; not evergreen;

Leaf quantity: About six per division and about 60 per plant;

Veins: Palmate; sparsely puberulent adaxial and abaxial;

Vein color: Adaxial early season main veins nearest RHS 148C and secondary veins nearest RHS 138B, abaxial early season main veins nearest RHS N148C, secondary veins nearest RHS 137C; flowering season through autumn adaxial proximal main veins nearest RHS 146D and distal secondary veins between RHS NN137A and RHS NN137B, flowering season through autumn abaxial main veins between RHS 146D and RHS 147C, secondary veins nearest 137B;

Petiole: Cylindrical; sparsely pubescent; aspect upwardly and outwardly; base amplexicaul with stipule; straight, stiff; to about 12 cm long and 3 mm diameter above stipule; stipule to about 14 mm long and 9 mm wide with two distal lobes about 2 mm across;

Petiole color: Variable; on emerging foliage in the distal 3 cm between RHS 146D and RHS 145C and proximally nearest RHS 148B with a slight blush of nearest RHS 183C; mid-flowering season through autumn nearest RHS 147C with a blush proximally of nearest RHS 183C where exposed to high light; stipule nearest RHS 145B;

Inflorescence: In open narrowly-branched panicles; to about 10 panicles per plant; to about 180 flowers per panicle; first panicle flowering beginning late May in Michigan and remaining in flower for about three weeks; repeat panicles if deadheaded;

Branches: To about 48; cylindrical; puberulent; aspect ascending; proximal branches to about 16 cm long and 1.5 mm diameter at base; distal branches significantly shorter; color nearest RHS 187A;

Fragrance: None detected;

Peduncle: Cylindrical; hirsutulous to pubescent with hairs to about 2 mm long; to about 50 cm tall and 3 mm diameter at base, flowering portion about 20 cm tall and 4.5 cm wide; with cauline leaves at lower two to four nodes; mostly ascending; flower density medium;

Peduncle color: Nearest RHS 187A;

Pedicel: Cylindrical; glandular to puberulent; to about 2 mm long and 0.5 mm diameter;

Pedicel color: Nearest RHS 187B;

Buds one day prior to opening: Oblong elliptical; about 4 mm long and 2.5 mm diameter;

Bud color: Distal two-thirds between RHS 63C and RHS 63D, proximal portion nearest RHS 187C;

Flower: Perfect; complete; campanulate; about 6.5 mm deep and 8 mm in diameter at face; individual flowers lasting about three to five days on plant or as cut flower; aspect outwardly to slightly drooping;

Calyx: Five sepals; about 8 mm across and 6.5 mm deep; fused in basal 4 mm into hypanthium;

Sepals: Lanceolate; glabrous adaxial, glandular abaxial; apex acute, margin entire; to about 6.5 mm long and 2.5 mm wide;

Calyx color: Middle portion adaxial and abaxial between RHS 63D and RHS 64D with the apical 1 mm between RHS 64C and RHS 64B and abaxial base nearest RHS 187C;

Petals: Typically, five; spatulate, narrowly acute apex, narrowly attenuate base; margin entire; glabrous abaxial and adaxial; about 5.5 mm long and 0.8 mm wide;

Petal color: Adaxial and abaxial nearest RHS NN155C;

Androecium:

*Filaments*.—Typically, ten; thin; about 5 mm long and less than 0.3 mm in diameter; color nearest RHS NN155B.

*Anthers*.—Vestigial; oblong to nearly 0.7 mm long and about 0.4 mm wide; color nearest RHS 155B.

*Pollen*.—Not observed.

Gynoecium:

*Pistil*.—One central two-beaked pistil, about 5 mm long.

*Stigma*.—Minute, about 0.2 mm diameter; color nearest RHS NN155C to transparent.

*Ovary*.—Two carpels; apex tapering to meet pistil; rounded base and sides; to about 1.5 mm diameter at base and about 1 mm tall; color nearest RHS 155B.

*Style*.—About 4 mm long; narrowing to 0.1 mm at stigma; color nearest RHS 155C.

Fruit: Not observed;

Seed: Not observed;

Growth conditions: X *Heucherella* 'Shadow Tag' grows best with ample moisture and drainage in either filtered or part sun. Winter hardy from USDA zones 4 to 9. 'Shadow Tag' is able to tolerate heat and humidity better than many x *Heucherella*.

Disease and pest tolerance: Other pest and disease resistance and tolerance outside of that normal for x *Heucherella* is not known. The new plant may be susceptible to diseases and pests common to other x *Heucherella*.

It is claimed:

1. The new and distinct ornamental x *Heucherella* plant named 'Shadow Tag' as herein described and illustrated.

* * * * *